United States Patent [19]

Millauer et al.

[11] Patent Number: 4,476,058
[45] Date of Patent: Oct. 9, 1984

[54] FLUOROSULFATOPERFLUOROALKANE-SULFONIC ACID HALIDES

[75] Inventors: Hans Millauer, Eschborn; Werner Schwertfeger, Butzbach, both of Fed. Rep. of Germany

[73] Assignee: Hoechst Aktiengesellschaft, Frankfurt am Main, Fed. Rep. of Germany

[21] Appl. No.: 496,633

[22] Filed: May 20, 1983

Related U.S. Application Data

[62] Division of Ser. No. 300,916, Sep. 10, 1981, abandoned.

[30] Foreign Application Priority Data

Sep. 12, 1980 [DE] Fed. Rep. of Germany ....... 3034550

[51] Int. Cl.³ .............................................. C07C 141/02
[52] U.S. Cl. .............................. 260/458 F; 260/543 F; 204/59 F; 204/72; 204/79
[58] Field of Search ...................................... 260/458 F

[56] References Cited

PUBLICATIONS

Ermolov et al., Zh. Org. Khim., 17, 2239, (1981), (Chem. Abstract, 96, 68269g (1981)).

*Primary Examiner*—Nicky Chan
*Attorney, Agent, or Firm*—Curtis, Morris & Safford

[57] ABSTRACT

A fluorosulfatoperfluoroalkanesulfonic acid halide of the formula

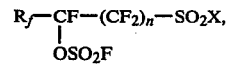

wherein $R_f$ is F or perfluoroalkyl having 1–10 carbon atoms, X is Cl or F, and n is a number from 0 to 7.

6 Claims, No Drawings

FLUOROSULFATOPERFLUOROALKANESULFONIC ACID HALIDES

This is a division of application Ser. No. 300,916 filed Sept. 10, 1981, now abandoned.

Perfluorocarbonyl compounds are chiefly intermediates in organic fluorine chemistry.

For example, they can be reacted with hexafluoropropene epoxide to give perfluorocarboxylic acid fluorides, which, when subjected to pyrolysis, give perfluorinated vinyl compounds:

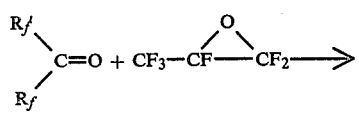

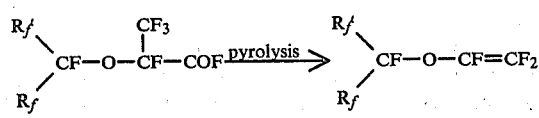

$R_f$=perfluoroalkyl and $R_f'$=fluorine or perfluoroalkyl.

Perfluorinated allyl ethers can also be prepared from perfluorocarbonyl compounds (German Offenlegungsschrift No. 2,753,886):

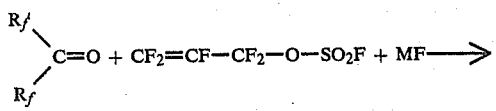

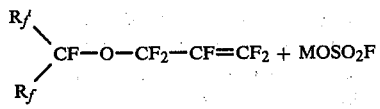

$R_f$=perfluoroalkyl, $R_f'$=fluorine or perfluoroalkyl and M=an alkali metal.

The perfluorinated vinyl or allyl ethers can be converted by homopolymerization or copolymerization into valuable oligomers and polymers which are exceptionally stable to chemicals and heat. The oligomers with a liquid consistency are used, for example, as lubricants and anti-friction agents and as hydraulic fluids, and the polymers with a solid consistency are used, inter alia, as coating materials, elastomers, ion exchangers (if acid or basic groups are also present) and the like.

Perfluorinated vinyl or allyl ethers with a sulfonic acid fluoride group have also already been prepared starting from perfluorocarbonyl compounds which also contain a sulfonic acid fluoride group, and, after copolymerization with tetrafluoroethylene and subsequent hydrolysis of the —SO₂—F group, gave a cation exchanger resin.

Thus, for example, the process described in U.S. Pat. No. 3,301,893 and U.S. Pat. No. 3,282,875 uses fluorosulfonyldifluoroacetic acid fluoride as the starting material. The reaction with hexafluoropropene epoxide and subsequent pyrolysis gives a perfluorinated vinyl ether with a sulfonic acid fluoride group:

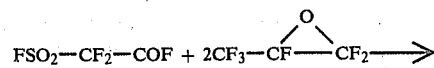

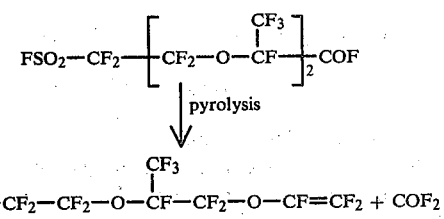

$$FSO_2-CF_2-CF_2-O-\underset{\underset{CF_3}{|}}{CF}-CF_2-O-CF=CF_2 + COF_2$$

The vinyl ether is copolymerized with tetrafluoroethylene. Hydrolysis of the copolymer can give the cation exchanger resin.

The reaction of 2-oxopentafluoropropanesulfonic acid 1,1-difluoroethyl ester with potassium fluoride and perfluoroallylfluorosulfate is described in German Offenlegungsschrift No. 2,753,886:

$$CF_3-CO-CF_2-SO_2-O-CF_2-CH_3 + KF +$$

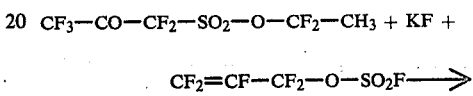

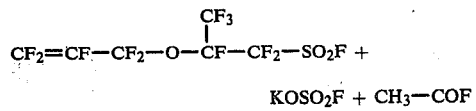

$$KOSO_2F + CH_3-COF$$

2-Oxopentafluoropropanesulfonic acid fluoride (CF₃—CO—CF₂—SO₂F) occurs as an intermediate in this reaction.

The resulting perfluorinated allyl ether with a sulfonic acid fluoride group is copolymerized with tetrafluoroethylene, and the resulting copolymer is hydrolyzed to give an ion exchanger resin.

The perfluorinated carbonyl compounds with a sulfonic acid fluoride group which are used as starting materials in these processes can be prepared by various methods.

For example, fluorosulfonyldifluoroacetic acid fluoride is obtained by reaction of tetrafluoroethylene with sulfur trioxide and rearrangement of the resulting sultone with triethylamine [J. Am. Chem. Soc. 82, 6181 (1960)]:

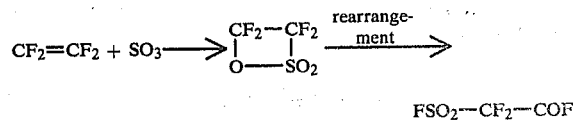

$$FSO_2-CF_2-COF$$

Preparation of the sultone is, however, associated with the danger of explosion, because sulfur trioxide can produce an exothermic reaction with the sultone already formed [Chem. Eng. News 49, Volume 22, page 3 (1971)]:

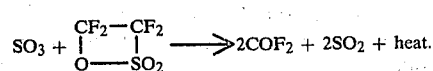

2-Oxopentafluoropropanesulfonic acid fluoride has not yet been isolated. However, it is reported that the compound is formed during the reaction of 2-oxopentafluoropropanesulfonic acid 1,1-difluoroethyl ester with potassium fluoride (German Offenlegungsschrift No. 2,753,886):

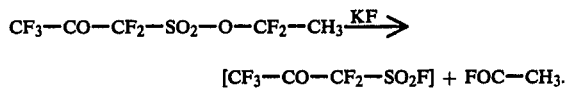

[CF₃—CO—CF₂—SO₂F] + FOC—CH₃.

2-Oxopentafluoropropanesulfonic acid 1,1-difluoroethyl ester, which decomposes in glass vessels and must therefore be stored in polyethylene bottles, is prepared by the following route:

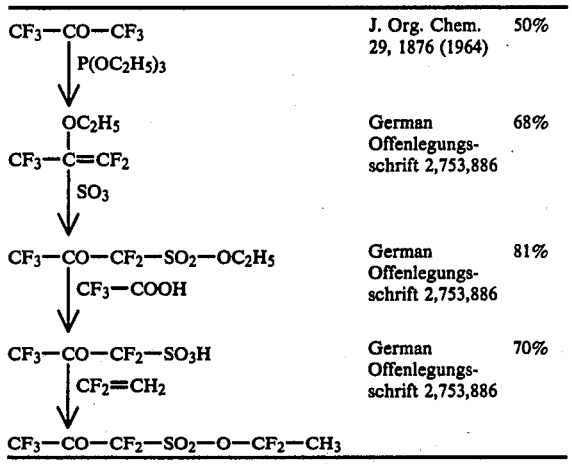

| | | |
|---|---|---|
| | J. Org. Chem. 29, 1876 (1964) | 50% |
| | German Offenlegungsschrift 2,753,886 | 68% |
| | German Offenlegungsschrift 2,753,886 | 81% |
| | German Offenlegungsschrift 2,753,886 | 70% |

The object of this invention was thus to discover a simple route, which is generally applicable and not dangerous, for the preparation of perfluorocarbonylsulfonic acid fluorides.

The invention relates to a process for the preparation of perfluorocarbonyl-sulfonic acid fluorides of the formula I:

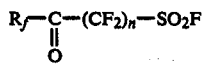

in which $R_f$ denotes F or perfluoroalkyl with 1-10, preferably 1-8 and in particular 1-3, C atoms and n denotes a number from 0 to 7, which comprises (a) electrolyzing monohydroperfluoroalkanesulfonic acid halides of the formula II

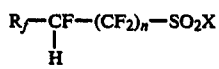

in which $R_f$ and n have the same meaning as in formula I and X denotes chlorine or fluorine, preferably fluorine, in an electrolyte consisting of fluorosulfonic acid and an alkali metal fluorosulfonate, using anodes of glassy carbon and cathodes of a material which is customary, but stable under the electrolysis conditions, and (b) reacting the fluorosulfatoperfluoroalkanesulfonic acid halides thereby obtained, of the formula III

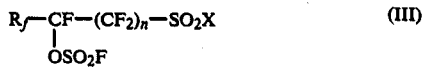

in which $R_f$, X and n have the same meaning as in the formulae I and II, in the presence of at least one alkali metal fluoride, to give the perfluorocarbonylsulfonic acid fluorides of the formula I.

The starting compounds of the formula II (in which n=a number from 1 to 7) required for the process according to the invention can be obtained by the process of U.S. Pat. No. 4,343,749, by the following route:

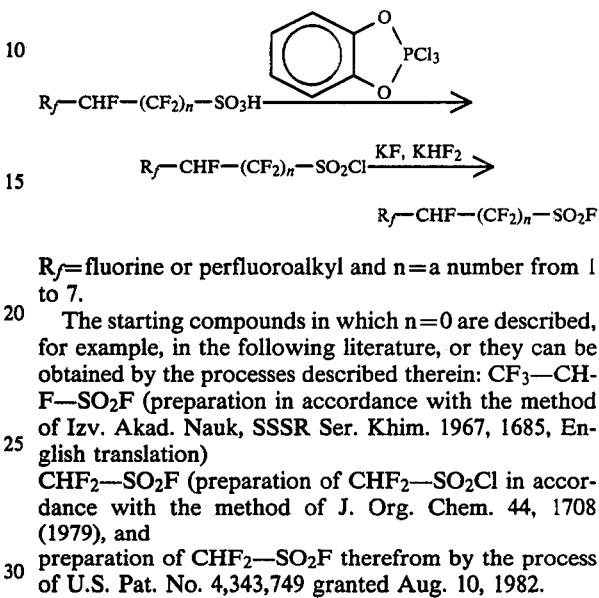

$R_f$=fluorine or perfluoroalkyl and n=a number from 1 to 7.

The starting compounds in which n=0 are described, for example, in the following literature, or they can be obtained by the processes described therein: CF₃—CHF—SO₂F (preparation in accordance with the method of Izv. Akad. Nauk, SSSR Ser. Khim. 1967, 1685, English translation)

CHF₂—SO₂F (preparation of CHF₂—SO₂Cl in accordance with the method of J. Org. Chem. 44, 1708 (1979), and preparation of CHF₂—SO₂F therefrom by the process of U.S. Pat. No. 4,343,749 granted Aug. 10, 1982.

Stage (a) of the process:

The preparation of the fluorosulfatoperfluoroalkanesulfonic acid halides, preferably the fluorides, of the formula III is carried out by anodic replacement of the hydrogen atom of the corresponding monohydroperfluoroalkanesulfonic acid halides, preferably the fluorides, of the formula II.

Such replacement reactions have already been described for polyfluorinated compounds with a primary hydrogen atom (—CHF₂). J. Chem. Soc. Chem. Comm. 1978, 118 describes anodic "functionalization" of 1-hydroperfluoroalkanes without another functional group in an electrolyte system of fluorosulfonic acid and potassium fluorosulfonate, as the conducting salt, in an undivided cell on platinum electrodes to give 1-fluorosulfatoperfluoroalkanes. The authors suppose the decisive intermediate to be peroxodisulfuryl difluoride (FSO₂—O—O—SO₂F), which is extremely reactive and is formed on the anode under the electrolysis conditions and, without being isolated, reacts with the fluorine compound present in the electrolyte.

The reaction of monohydroperfluoro compounds with pure peroxodisulfuryl difluoride has also already been described [J. Fluorine Chem. 2, 173 (1972/73)]. Under these conditions, it is even possible to replace hydrogen atoms in molecules which already contain a functional group, for example a nitrile group (yield: 22%). Nevertheless, the electrochemical method is generally to be preferred, since in this case the dangerous, separate preparation of peroxodisulfuryl difluoride from fluorine and sulfur trioxide is eliminated. In contrast, the reagent produced in situ in the electrochemical method needs to be present only in low, stationary concentrations and can be reacted without danger. However, the electrochemical method cannot be generally employed a priori, for example because of side reactions with the electrolyte or side processes on the cathode, especially in the case of compounds with another functional group. Thus, for example, it is not possible to introduce fluorosulfato groups into compounds with the abovementioned nitrile group by anodic replacement. In the case of the process according to the invention, however, the anodic replacement proceeds satisfactorily, although the anode material described in the state of the art proved to be unsuitable. These electrodes tend to have a relatively high degree of corrosion, the platinum removed remaining partly as a sludge and partly in solution. Partial redeposition of the platinum dissolved from the anode onto the cathode has a particularly adverse effect, leading to covering layers with a poor conductivity and to high cell voltages. The answer to this problem is based on the use of glassy carbon instead of platinum as the anode material. This material proves to be unexpectedly corrosion-resistant, although other carbon electrodes, such as electrode graphite or impregnated apparatus graphite, are instantaneously destroyed by the electrolyte, even if no current is flowing.

In addition to other substances, such as, for example, platinum or high-grade steel, glassy carbon is also suitable as the cathode material.

The electrolysis can be carried out in simple, undivided cells. Cells divided by porous diaphragms can improve the current efficiency, since they suppress undesired side reactions, such as, for example, resplitting of the peroxodisulfuryl difluoride at the cathode.

The ratio of the anode area to the cathode area is between about 1:1 to 10:1 . . . , preferably about 5:1 to 10:1.

The base electrolyte, which, according to the invention, consists of fluorosulfonic acid and an alkali metal fluorosulfonate dissolved therein, is advantageously prepared by dissolving a corresponding, readily accessible alkali metal chloride, such as, for example, lithium chloride, sodium chloride or potassium chloride, in fluorosulfonic acid, which, if necessary, has been subjected to purification by fractional distillation, most of the hydrogen chloride immediately escaping from the solution. The remainder is driven out by introduction of dry nitrogen. The concentration of alkali metal sulfonate to be used in the base electrolyte is not critical and is usually in the range from about 0.05 to about 3 moles per liter. If necessary, oxidizable impurities or traces of moisture are removed by preliminary electrolysis.

The monohydroperfluoroalkanesulfonic acid halides II used as starting substances are dissolved or dispersed in the base electrolyte, mixtures containing up to about 60% of the starting compound, relative to the base electrolyte, being used. The electrolysis is advantageously carried out at an anodic current density of about 10-150 mA.cm$^{-2}$, preferably about 20-80 mA.cm$^{-2}$, and at a temperature of about 0°-100° C., preferably about 20°-40° C.

Working up of the electrolysis mixtures and isolation of the fluorosulfatoperfluoroalkanesulfonic acid halides are carried out in a manner known per se. In the case of two-phase reaction mixtures, it is advantageous to separate the fluoro-organic phase, which in some cases also contains a little fluorosulfonic acid, by decanting. Otherwise, the electrolysis product must be separated from the base electrolyte by distillation. In both cases, the electrolyte phase or the distillation bottom product can be recycled into the electrolysis stage again after addition of fresh fluorosulfonic acid.

The crude fluorosulfatoperfluoroalkanesulfonic acid halides can be further purified by fractional distillation yielding new compounds.

Stage (b) of the process:

According to the invention, perfluorocarbonyl compounds of the formula I which contain a sulfofluoride group are prepared from the fluorosulfatoperfluoroalkanesulfonic acid halides of the formula III by reaction with catalytic amounts of an alkali metal fluoride (LiF, NaF, KF, RbF or CsF). However, if X=Cl in formula III, at least an amount of alkali metal fluoride which is equimolar to the amount of III must additionally be employed.

The splitting of primary and secondary fluorosulfates with alkali metal fluorides has already been published several times: thus, for example, the decomposition of a molecule containing a primary and a secondary fluorosulfato group has been described in Inorg. Chem. 3, 287 (1964).

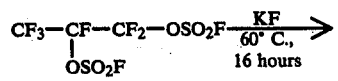

Only the primary fluorosulfato group is attacked. If CsF is used instead of KF, the entire molecule is destroyed. No amounts are given.

Primary and secondary fluorosulfates are also reacted with potassium fluoride in Inorg. Chem. 4, 1441 (1965).

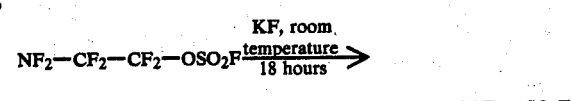

The potassium fluoride is employed in an approximately 50 molar excess, per mole of fluorosulfate, in these reactions.

J. Fluorine Chem. 14, 519 (1979) describes the reaction of primary fluorosulfates with cesium fluoride

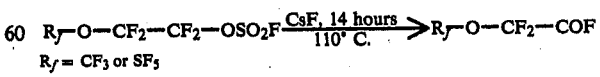

The fluorosulfate and the CsF are employed in a molar ratio of 1:20 in this reaction.

The decomposition of a secondary fluorosulfate described in Inorg. Chem. 18, 3281 (1979) is carried out with a large excess of KF. In addition, rearrangement also occurs in this case:

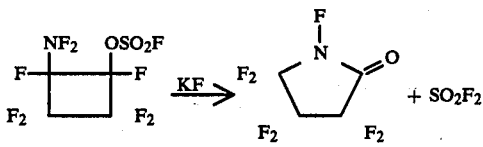

The decomposition of secondary fluorosulfates is also described in Inorg. Chem. 5, 2184 (1966)

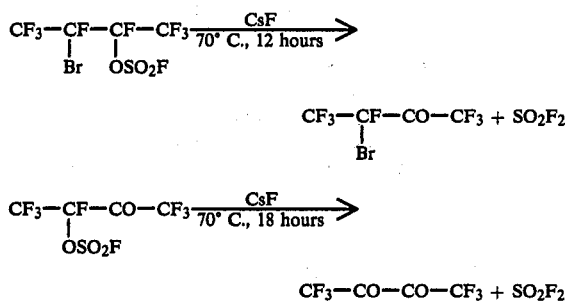

While a large excess of cesium fluoride is employed in the second case, no amounts are given in the first case. However, it must be assumed that, as is customary, a more than equimolar amount of the cesium fluoride, per mole of fluorosulfate, is used.

All these reactions have the common fact that they are carried out without a solvent. In these cases, a considerable excess of alkali metal fluoride seems necessary for the reaction to take place.

However, there are also examples of the use of catalytic or equimolar amounts of an alkali metal fluoride for such reactions, in particular if an aprotic solvent, such as diglyme or acetonitrile, is employed.

Such a reaction is described in Izv. Akad. Nauk SSSR, Ser. Khim. 1973, 2659 (English edition) for a primary fluorosulfate (with catalytic amounts of KF):

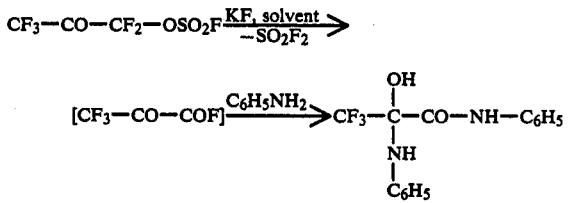

and in U.S. Pat. No. 3,549,711 for a secondary fluorosulfate (with equimolar amounts of KF)

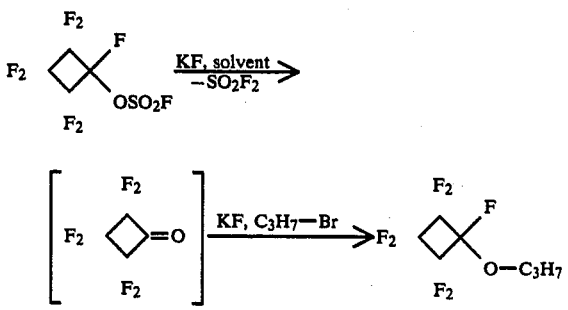

In these two cases, however, the perfluorocarbonyl compound formed is not isolated, but is further reacted directly, so it is still unclear whether it is possible to isolate the perfluorocarbonyl compounds at all under these conditions.

On the basis of the abovementioned literature examples for the splitting of primary and secondary fluorosulfates, it was thus surprising that fluorosulfates of the formula III can be converted into perfluorocarbonyl compounds containing a sulfofluoride group of the general formula I with catalytic to equimolar amounts of an alkali metal fluoride in the presence or absence of an aprotic polar solvent, and that the products can be isolated.

The alkali metal fluorides (LiF, NaF, KF, RbF or CsF) employed as catalysts for the process according to the invention can be used either individually or as mixtures with one another. The amount of catalyst is in general between about 1 and about 100 mole %, relative to the starting compound III (in which X=F). If a fluorosulfate of the general formula III (in which X=Cl) is employed, an amount of alkali metal fluoride equimolar to the amount of III must additionally be used, because the sulfochloride group is simultaneously converted into the sulfofluoride group.

The reaction can be carried out in the presence or absence of an aprotic polar solvent, such as acetonitrile, diglyme, tetraglyme, sulfolane, dimethylsulfoxide and the like.

The reaction temperatures are between about $-20°$ and about $+120°$ C., depending on the catalyst used and any solvent which may be used.

The sequence in which the reactants and any solvent which may be used are brought together is practically of no importance for the reaction according to the invention. Nevertheless, it is advantageous to ensure thorough mixing of the batch throughout the entire period of the reaction.

In a preferred embodiment, the alkali metal fluoride and any solvent which may be used are initially introduced into the reaction vessel and the fluorosulfate III is added dropwise. If the reaction does not already start during the dropwise addition, the mixture is heated until evolution of gas occurs. When the evolution of gas has ended, the batch is distilled.

The perfluorinated carbonyl compounds with a sulfofluoride group which are prepared by the process according to the invention are in general colorless liquids which are sensitive to moisture. They are therefore to be prepared in the absence of moisture. Of the compounds I, those in which n=a number from 2 to 7 are new (formula I' = formula I in which n=a number from 2 to 7).

The compounds I are chiefly processed, by known methods, to perfluorinated vinyl or allyl compounds which also have a sulfofluoride group in the molecule, these compounds in turn being converted into valuable homopolymers and copolymers. The homopolymers and copolymers are used, for example, (after hydrolysis of the sulfofluoride groups) as ion exchangers which are resistant to chemicals and heat.

The advance of the invention can be seen from the following comparison:

(1) Preparation of FOC—CF$_2$—SO$_2$F

Although the process according to the invention for the preparation of FOC—CF$_2$—SO$_2$F is inferior to the known process [J. Am. Chem. Soc. 82, 6181 (1960)] in respect of the number of reaction steps and the overall yield, it is nevertheless an improvement, because the reaction step in the known process which is associated with the danger of explosion is avoided.

(2) Preparation of $CF_3-CO-CF_2-SO_2F$

The process according to the invention enables $CF_3-CO-CF_2-SO_2F$ to be isolated for the first time. In addition, the precursor for the preparation of this compound can also be stored in glass vessels in a pure state. The overall yields, starting from hexafluoroacetone or hexafluoropropene, are approximately the same. However, it must be taken into consideration that hexafluoroacetone has to be prepared from hexafluoropropene. Because of the numerous published processes, only the one-stage processes in German Auslegeschrift No. 2,624,349 and German Auslegeschrift No. 2,738,010 are referred to here. In advantageous cases, a yield of up to ~70% of hexafluoroacetone is obtained in these processes, at conversions of 10-15 mole %.

The following comparison is intended to illustrate the route—starting from known simple "base products"—to the compound $CF_3-CO-CF_2-SO_2F$ according to the state of the art and according to the invention:

Known process (state of the art):

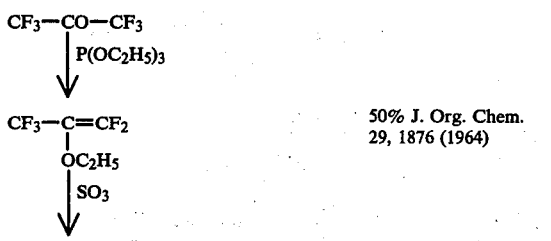

| | 50% J. Org. Chem. 29, 1876 (1964) |

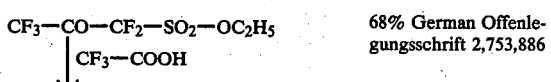

| | 68% German Offenlegungsschrift 2,753,886 |

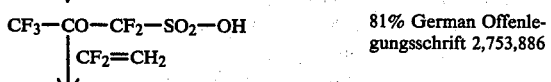

| | 81% German Offenlegungsschrift 2,753,886 |

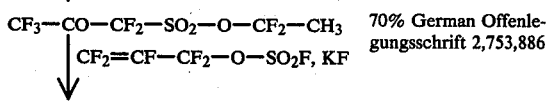

| | 70% German Offenlegungsschrift 2,753,886 |

| | 34% German Offenlegungsschrift 2,753,886 |

Overall yield up to precursor
$CH_3-CO-CF_2-SO_2-O-CF_2-CH_3$: 19%

Invention:

| | J. Am. Chem. Soc. 75, 4595 (1953) |

| | 64% (own yield: 70%) |

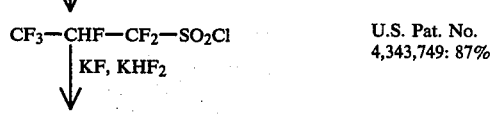

| | U.S. Pat. No. 4,343,749: 87% |

-continued

| $CF_3-CHF-CF_2-SO_2F$ | 61% according to the invention |
| $e^-$ ↓ $HSO_3F$, $KSO_3F$ | |
| $OSO_2F$ | 46% |
| $CF_3-\overset{\mid}{C}F-CF_2-SO_2F$ | |
| ↓ KF | |
| $CF_3-CO-CF_2-SO_2F$ | 46% |
| Overall yield up to precursor $OSO_2F$ $CF_3-\overset{\mid}{C}F-CF_2-SO_2F$: | 17% |

The invention will now be illustrated in more detail by the following examples:

EXAMPLE 1

Preparation of 2-fluorosulfato-perfluoroethanesulfonic acid fluoride

The electrolysis device comprises a cylindrical glass vessel which has an internal diameter of 60 mm and is about 100 mm in height and is provided with an outer cooling jacket and a lid. The cell is provided with a dry ice condenser, acting as a reflux condenser, a gas inlet tube, a thermometer and the current leads for the electrodes. The anode comprises a plate (100×20×3 mm) of glassy carbon which is attached to the lid of the cell and of which about 60 mm are immersed in the electrolyte. A 1.5 mm thick platinum wire arranged parallel to the anode at a distance of about 20 mm serves as the cathode. A bar magnet encased in PTFE is used as the stirrer. Perchloroethylene is used as the inert cooling liquid for the cooling jacket. All the components of the device which come into conctact with the medium are made of glass, platinum or PFTE.

The base electrolyte is prepared by adding 12.5 g of potassium chloride to 250 g of distilled fluorosulfonic acid. Hydrogen chloride is thereby formed and is driven out of the solution by introduction of dry nitrogen. The solution is then pre-electrolyzed at 2 A for about 4 hours.

After 120 g (0.65 mole) of 2-hydroperfluorobutanesulfonic acid fluoride have been added, electrolysis is carried out at a current strength of 3 A and a cell voltage of 18 to 22 V until the charge which has been put through is 70 Ah. The reaction temperature is 25°-30° C.

The electrolysis mixture is then separated into its components in a separating funnel and the fluoroorganic phase is subjected to fractional distillation. 110 g of a fraction of boiling point 87°-90° C. which consists of 2-fluorosulfato-perfluoroethanesulfonic acid fluoride to the extent of 95% are obtained, which corresponds to a yield of about 54%, relative to the material employed.

$^{19}F$-NMR ($CDCl_3$)*: +52.7 (1F, $-O-SO_2-F$), +47.27 (1F, $-SO_2-F$), -81.45 (2F, $-CF_2-O$), -111.0 (2F, $-CF_2-S$). *) $CFCl_3$ is used as the internal standard in all the $^{19}F$-NMR spectra.

EXAMPLE 2

Preparation of
2-fluorosulfato-perfluoropropanesulfonic acid fluoride (CF$_3$—CF(OSO$_2$F)—CF$_2$—SO$_2$F)

Using an electrolysis device and after preparation of a base electrolyte as described in Example 1, 133 g (0.57 mole) of 2-hydroperfluoropropanesulfonic acid fluoride are electrolyzed at a current strength of 2 A and a cell voltage of 12–24 volts for 45 hours. The temperature is 30°–35° C. The fluoro-organic phase is separated off from the electrolyte by decanting and is subjected to fractional distillation. 123 g of a fraction of boiling point 105° C. which, according to the $^{19}$F-NMR spectrum, contains 70% of 2-fluorosulfatoperfluoropropanesulfonic acid fluoride (in addition to 30% of 1,2-difluorosulfato-perfluoropropane) are obtained.

$^{19}$F-NMR (CDCl$_3$): +53.09 (1F, O—SO$_2$—F), +47.8 (1F, —SO$_2$F), −76.14 (3F, —CF$_3$), −106.0 (2F, —CF$_2$—SO$_2$—), −135.3 (1F,

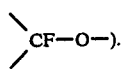).

EXAMPLE 3

Fluorosulfonyldifluoroacetic acid fluoride

F—SO$_2$—CF$_2$—COF

The reaction is carried out in a fume cupboard.

3 g (0.02 mole) of cesium fluoride and 30 ml of tetraethylene glycol dimethyl ether are initially introduced into a dry flask with a magnetic stirrer, thermometer, dropping funnel, reflux condenser, which is kept at about −30° C., and subsequent bubble counter. 48 g (0.17 mole) of 2-fluorosulfatoperfluoroethanesulfonic acid fluoride are added dropwise at an internal temperature of 15°–20° C. Evolution of gas (SO$_2$F$_2$) starts immediately. When the evolution of gas has ended, the batch is warmed to 25°–30° C. and is kept at this temperature for about 30 minutes. Subsequent distillation gives 18.8 g (61%) of fluorosulfonyldifluoroacetic acid fluoride with a boiling point of 29°–30° C. (760 mm). The spectral data (IR and $^{19}$F-NMR spectrum) of the compound agree with the structure given.

EXAMPLE 4

2-Oxoperfluoropropenesulfonic acid fluoride

CF$_3$—CO—CF$_2$—SO$_2$F

The reaction is carried out in a fume cupboard.

8.7 g (0.15 mole) of potassium fluoride are initially introduced into a dry flask with a magnetic stirrer, dropping funnel, thermometer, reflux condenser, bubble counter and subsequent cold trap (−78° C.), and 50 g (∼0.15 mole) of the substance mixture from Example 2 are then added dropwise. The batch is warmed. A vigorous reaction suddenly starts at an internal temperature of about 95°–100° C. A large quantity of gas condenses in the cold trap. When the reaction has ended, the cold trap is allowed to warm to room temperature. The liquid which then remains is distilled with the contents of the flask. 13.2 g (46%, relative to the CF$_3$CF(OSO$_2$F)—CF$_2$—SO$_2$F contained in the starting mixture) of 2-oxoperfluoropropanesulfonic acid fluoride with a boiling point of 49°–50° C. (755 mm) are obtained.

$^{19}$F-NMR (CDCl$_3$): +44.5 (1F, —SO$_2$F), −74.6 (3F, CF$_3$), −104.2 (2F, CF$_2$).

We claim:

1. A fluorosulfatoperfluoroalkanesulfonic acid halide of the formula

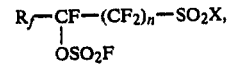

wherein R$_f$ is F or perfluoroalkyl having 1–10 carbon atoms, X is Cl or F, and n is a number from 0 to 7.

2. An acid halide as in claim 1 wherein X is F.
3. An acid halide as in claim 1 wherein said perfluoroalkyl has 1–8 carbon atoms.
4. An acid halide as in claim 3 wherein X is F.
5. An acid halide as in claim 1 wherein said perfluoroalkyl has 1–3 carbon atoms.
6. An acid halide as in claim 5 wherein X is F.

* * * * *